United States Patent [19]

Harper et al.

[11] Patent Number: 5,730,845
[45] Date of Patent: Mar. 24, 1998

[54] METHOD AND APPARATUS OF PRODUCING AN ORGANO-NITROGEN COMPOUND

[75] Inventors: David John Harper, Le Masnau, Massuguis, France; Ronald Michael Henson, Stafford; David John Wheeler, Leicester, both of United Kingdom

[73] Assignees: Gecalsthom Limited; Isambard Services Limited, both of United Kingdom

[21] Appl. No.: 643,866

[22] Filed: May 7, 1996

[30] Foreign Application Priority Data

May 11, 1995 [GB] United Kingdom ............... 9509563

[51] Int. Cl.$^6$ ........................... C07C 1/00
[52] U.S. Cl. ............... 204/157.64; 502/336; 558/316
[58] Field of Search ............... 502/326, 336; 558/319, 320, 327, 316; 204/157.64

[56] References Cited

U.S. PATENT DOCUMENTS

| | | | |
|---|---|---|---|
| 3,716,496 | 2/1973 | Yoshino et al. | 502/215 |
| 3,755,199 | 8/1973 | Stefanescu et al. | 502/243 |
| 3,927,007 | 12/1975 | Lussling et al. | 546/286 |
| 4,309,361 | 1/1982 | Suresh et al. | 558/324 |
| 4,767,739 | 8/1988 | Glaeser et al. | 502/209 |
| 4,866,024 | 9/1989 | Brazdil et al. | 502/209 |
| 4,877,764 | 10/1989 | Glaeser et al. | 502/209 |
| 5,015,349 | 5/1991 | Suib et al. | 204/168 |
| 5,131,993 | 7/1992 | Suib et al. | 204/168 |

OTHER PUBLICATIONS

Bulletin De La Societe Chimique De France, Partie I, 1979 Paris, FR, pp. I-320–I-324 XP002008930, C. Lalo, et al., *Synthese de l'ammoniac par excitation micro-ondes de melanges gazeux d'azote et d'hydrogen. Etude en phase homogene et en presence d'une phase solide*, pp. I-320 –I-321, *Dispositif experiemental*, pp. I-321 –I-323, *Effet heterogene*.

Primary Examiner—C. Warren Ivy
Assistant Examiner—Garth M. Dahlen
Attorney, Agent, or Firm—Kirschstein, et al.

[57] ABSTRACT

A method of producing an organo-nitrogen compound by the direct conversion of elemental nitrogen, in which a substrate vapor of a simple organic compound, e.g. propanol is mixed with a carrier gas at least partly comprising nitrogen and the vapor mixture is passed over a catalyst, e.g. of a transition metal, and irradiated with microwave radiation to produce a simple organo-nitrogen compound.

17 Claims, No Drawings

METHOD AND APPARATUS OF PRODUCING AN ORGANO-NITROGEN COMPOUND

BACKGROUND OF THE INVENTION

This invention relates to a method and apparatus for producing an organo-nitrogen compound, particularly by the direct conversion of elemental nitrogen. The preparation of such compounds generally originates with inorganic nitrogen compounds such as the nitrogen oxides, nitric acid and ammonia. These inorganic nitrogen compounds are bulk commodity chemicals and are manufactured on a huge scale, providing the basic raw materials for a huge range of products produced by the agrochemical, pharmaceutical and dyestuffs sectors of the international chemical industry. However, because of the low reactivity of elemental nitrogen, high temperatures and pressures are normally required together with expensive catalysts based on platinum group metals to convert elemental nitrogen into the above inorganic compounds. This involves intensive capital investment in the plant used for production of such materials and consequently very great expense in view of the enormous quantities of material required.

The object of the present invention is to provide a method of preparation of organo-nitrogen compounds by direct conversion of elemental nitrogen.

SUMMARY OF THE INVENTION

According to one aspect of the invention, in a method of producing an organo-nitrogen compound a substrate vapour comprising an organic compound is mixed with elemental nitrogen, and the mixture is passed in contact with a catalyst while the catalyst is irradiated with microwave radiation.

The catalyst may include a catalytic material which is an oxide of a transition element, an oxide of two or more transition elements or a mixture of at least two oxides of transition elements. The transition element preferably has an atomic number from 22 to 29 or from 40 to 47.

The catalytic material may be an oxide of at least one metal selected from a group consisting of Fe, Ni, Co and Cu and may be $Fe_3O_4$ or $Fe_{(1-x)}Ni_xOFe_2O_3$.

The catalyst may include a ceramic substrate having a coating of said catalytic material deposited on the surface thereof. Alternatively, the catalyst may include solid particles of catalytic material compacted together to form a porous bed.

The mixture of substrate vapour and nitrogen may further include $O_2$ and/or $H_2O_2$. The substrate material preferably comprises substrate molecules each having hydrogen atoms plus no more than six atoms all of which may be carbon and no more than three of which are selected from oxygen, sulphur, phosphorous and nitrogen.

The microwave field may be applied cyclically or intermittently to the catalyst the duration of the 'On' and 'Off' cycles being controlled to achieve a predetermined heating rate and temperature of the catalyst.

DETAILED DESCRIPTION OF THE INVENTION

A method of producing an organo-nitrogen compound in accordance with the invention will now be described, by way of example only.

In this particular embodiment a catalyst is formed as a coating on a ceramic mesh. The ceramic mesh provides mechanical stability while at the same time affording a large surface area. The nature of the underlying ceramic is not important and may be chosen for reasons of ease of manufacture for example. Alumina is a suitable material. The catalytic material itself is suitably magnetite ($Fe_3O_4$) applied in the form of finely divided particles suspended in a liquid organic matrix. This suspension is applied to the surface of the ceramic mesh, dried and fired to obtain a suitably thick coating of magnetite catalyst. Several such coats may be applied in this way to obtain a sufficient coating thickness in the range 10–100 microns. The deposition of catalyst from a particle suspension in this way provides a very high catalytic surface area.

The ceramic mesh coated with catalyst is arranged in a duct so as to intercept vapour passed through it. The mesh may be one of a series of similarly coated mesh elements so increasing the interaction between vapour and catalyst. The duct may be one of several in parallel to increase the vapour throughput.

The vapour that is passed through the duct consists of a substrate vapour mixed with a carrier gas. The latter essentially contains nitrogen and in this example contains oxygen. The substrate vapour is 1-propanol and the overall proportions in the mixed carrier gas and substrate vapour are: nitrogen 90 to 99%; oxygen 0 to 1% and propanol 1 to 10%. The vapour mixture is then blown through the catalyst-loaded duct.

The duct has a window, either for each ceramic mesh, or common to all of the ceramic meshes, the window(s) being transparent to microwave radiation. A microwave source operating at 2.45 GHz and a power level in the range 0.1 to 1.0 watts/square centimeter of the catalyst surface area produces a catalyst temperature in the range 100° C. to 200° C. The power level of the source is controlled to produce a catalyst temperature stabilized within ±10° C. in this range. A temperature sensor is incorporated in the ceramic mesh for this purpose.

In the present embodiment the microwave power and duct dimensions are such that a vapour flow rate up to 1 liter per minute per square centimeter of cross section of the catalyst bed achieves the required temperature at the catalyst surface.

The gases/vapour exiting the catalyst-bed duct are passed through a condenser and cooled to below ambient temperature and preferably to a temperature in the range −15° C. to 0° C. This causes the reaction products and any unreacted propanol to condense to form a liquid mixture, the components of which are separated by fractional distillation or other convenient means.

In the present example using a carrier gas of nitrogen plus a small proportion of oxygen as indicated above, a substrate vapour of 1-propanol and $Fe_3O_4$ as a catalyst, the reaction product will be a mixture of heterocyclic and alicyclic nitrogen containing organic compounds.

While a specific process has been described above, many variations are possible.

CATALYST

Certain transition metal oxides, including oxides in which more than one metal is present, either as simple mixtures or constituting a single compound, interact or absorb microwave radiation in the range 1–20 GHz. This is dependent, in part, on the said oxides possessing readily mobilized electrons in a conduction (or semi conduction) band. Thus, by irradiating such materials with microwaves the kinetic energy of the electrons is enhanced by the high voltages induced in the metal oxide by the microwave field and further by the oscillating electrical and/or magnetic fields generated by the microwaves. When endowed with sufficient energy, such electrons are able to participate in chemical reactions by electron-transfer to molecules either in the gaseous phase in contact with the surface of the metal oxide, or absorbed onto the catalyst surface from the gaseous phase. The electron transfer is able to generate a range of reactive chemical intermediates, depending on the precise composition and nature of the organic substrates in the gaseous phase, such as free radical anions, which are able to undergo a variety of complex reactions.

A particular aspect of the invention is the use of various catalysts either singly or in combination, at least one of which is capable of suscepting microwave radiation in the range 1–20 GHz. In general these catalysts are transition metal oxides, i.e. oxides or mixed oxides of metals from the first transition series (i.e. having atomic numbers 22 to 29 inclusive) and/or the second transition series (i.e. having atomic numbers 40 to 47 inclusive). Thus the catalyst may be a layer of magnetite ($Fe_3O_4$) or an analogue in which part of the Ferrous ion complement has been replaced by another transition metal ion, such as nickel, cobalt or copper, the empirical formula being represented $(Fe_{(1-x)}Ni_xO).Fe_2O_3$. The thickness of the catalyst layer is preferably of the order of 10–100 microns.

The catalysts may be in the form of:

(i) Particulate solids, packed together to form a porous bed.

(ii) A coating formed on a ceramic body. The latter may be in any morphological form affording reasonable mechanical stability and presenting a large surface area relative to its density. This may be in the form of a collection of small shapes, such as open-ended cylinders, spirals, etc., which may be packed together to form a porous bed. Alternatively the ceramic material may be formed from a monolithic structure, such as a mesh (as employed in the specific embodiment described above) or a foam having an open celled structure.

The coating may be formed on the surface by a variety of methods, such as preparing an ink or paint of the catalyst by suspending finely divided particles in a liquid organic matrix, applying this to the surface of the ceramic body, drying and subsequently firing to obtain a suitably catalyst coating; this may require more than one application of the paint.

ORGANIC SUBSTRATES

The organic chemical forming the substrate vapour may be a saturated or unsaturated aliphatic or aromatic hydrocarbon, an aliphatic or aromatic alcohol, ketone, carboxylic, sulphonic, sulphinic, or phosphonic acid or their esters, in fact any preferably simple, organic vapour or volatile liquid which may or may not contain nitrogen. Since the complexity of the process and of the intermediate products increase with the complexity of the substrate material it is desirable to restrict the substrate molecule to one having, in addition to hydrogen atoms, no more than six other atoms all of which may be carbon and up to three of which may be selected from oxygen, sulphur, phosphorus and nitrogen. The organic substrate is presented to the catalyst as a vapour mixed with a carrier gas containing nitrogen in the range 1 to 100%. The vapour mixture may be formed by a variety of methods, for example by passing a stream of gaseous nitrogen through the organic substrate under controlled conditions of temperature and flow rate, or introducing a spray of the substrate into the nitrogen gas. The resulting gaseous mixture is then passed over the catalyst bed during irradiation of the latter by a microwave field. Further examples of organic substrate are as follows:

methane, ethane, propane, butane or other aliphatic alkanes; ethylene, propylene or other aliphatic alkanes; acetylene; methanol, ethanol, 1-propanol, 1-butanol, 2-butanol, or other aliphatic alcohols; formaldehyde, acetaldehyde, 1- or 2-propanone, 2-butanone, or other carbonyl compounds; formic acid, acetic acid or other aliphatic carboxylic acids; benzene, xylene and toluene or other aromatic hydrocarbons, or various of their substituted derivatives, such as phenols, acyl derivatives.

CARRIER GAS

This may be 100% nitrogen, or nitrogen in admixture with other gases such as hydrogen, helium, argon such that the nitrogen concentration is in the range 1–100%. For some reactions it is essential that some elemental oxygen and/or hydrogen peroxide is present, in the range 0.001 to 1%.

MICROWAVE IRRADIATION

This may be any one, or a combination of frequencies from 1 to 20 GHz in frequency. For the purpose of the invention the microwave frequency and intensity are matched to the catalyst bed so that the latter uniformly suscepts the microwave field so far as the permeability, thickness and morphology of tile catalyst allows, and that the temperature of the bed is reasonably homogeneous on the macro scale (as opposed to the molecular, atomic or electronic scales). Such tuning can be achieved by matching the morphology and permeability of the catalyst bed to the microwave field, which itself can be modified by appropriate design of a suitable horn and waveguide.

It is preferred that the microwave field be applied continuously to the catalyst bed, but it is also a feature of this invention that a temperature sensing system may be used to determine the average temperature of the catalyst bed and of a representative set of sampling positions within it. The temperature sensing system is linked to an electrical system controlling and feeding the microwave generator to facilitate rapid switching on and off, for discrete periods, of the microwave field to match energy input to the desired temperature and substrate flow rates.

The essential requirement here is that the whole of the gaseous organic substrate passed over the catalyst will contact part of the catalyst synchronously with the absorption of microwave radiation and will not be subjected to temperatures significantly in excess of 200° C.

It may be seen that by careful selection of catalyst properties, the type, identity and concentration of the substrate vapour (organic compound) and the concentration of the carrier gas, i.e. nitrogen gas (and also, for some reactions, elemental oxygen) it is possible to produce compounds ranging from, for example, very simple nitrogen compounds to highly complex nitrogen containing heterocyclic compounds. Some examples of reaction products available are: 1- and 2-napthylamines, pyrole and pyridine derivatives, hydrocyanic acid, various secondary aliphatic amines and aliphatic heterocyclic nitrogen compounds.

A particular advantage of the invention is that the synthesis of organo-nitrogen compounds from elemental nitrogen is achieved at ambient atmospheric pressures, relatively low temperatures and inexpensive catalysts based on, typically, transition metal oxides.

We claim:

1. A method of producing an organo-nitrogen compound comprising the steps of: selecting a catalyst capable of suscepting microwave radiation in a range 1–20 GHz; mixing an organic compound with elemental nitrogen to form a mixture; and passing the mixture in contact with the catalyst while the catalyst is irradiated with the microwave radiation.

2. The method according to claim 1, in which the catalyst includes a catalytic material which is an oxide of a transition element, an oxide of two or more transition elements, or a mixture of at least two oxides of transition elements.

3. The method according to claim 2, in which the transition element has an atomic number from 22 to 29 or from 40 to 47.

4. The method according to claim 2, in which the catalytic material is an oxide of at least one metal selected from a group consisting of Fe, Ni, Co and Cu.

5. The method according to claim 2, in which the catalytic material is $Fe_3O_4$ or $Fe_{(1-x)}Ni_xOFe_2O_3$.

6. The method according to claim 2, in which the catalyst includes a ceramic substrate having a coating of said catalytic material deposited on a surface thereof.

7. The method according to claim 2, in which the catalyst includes solid particles of said catalytic material compacted together to form a porous bed.

8. The method according to claim 1, in which the mixture further includes $O_2$ and/or $H_2O_2$.

9. The method according to claim 8, in which said mixture includes up to 1% oxygen.

10. The method according to claim 1, wherein the organic compound has molecules each having hydrogen atoms plus no more than six atoms all of which may be carbon and no more than three of which are selected from oxygen, sulphur, phosphorus and nitrogen.

11. The method according to claim 1, in which the microwave radiation is applied cyclically or intermittently to said catalyst during on and off cycles controlled in duration to achieve a predetermined heating rate and temperature of the catalyst.

12. The method according to claim 1, and further comprising the step of controlling the temperature of the catalyst such that the substrate vapour will not be subjected to temperatures significantly in excess of 200° C.

13. A method of producing an organo-nitrogen compound from a mixture of an aliphatic compound and elemental nitrogen, the method comprising the steps of: passing the mixture along a flow path where the mixture contacts a catalyst while irradiating the catalyst with microwave radiation.

14. A method of producing an organo-nitrogen compound from a mixture of an alcohol and elemental nitrogen, the method comprising the steps of: passing the mixture along a flow path where the mixture contacts a catalyst while irradiating the catalyst with microwave radiation.

15. A method of producing an organo-nitrogen compound comprising the steps of: mixing 1-propanol with elemental nitrogen to form a mixture, and passing the mixture over a catalyst while the catalyst is irradiated with microwave radiation.

16. A method of producing an organo-nitrogen compound comprising the steps of: selecting a catalyst capable of suscepting microwave radiation in a range 1–20 GHz; mixing an organic compound with elemental nitrogen and a substance selected from the group consisting of oxygen and hydrogen peroxide to form a mixture; and passing the mixture in contact with the catalyst while the catalyst is irradiated with the microwave radiation.

17. A method of producing an organo-nitrogen compound comprising the steps of: selecting a catalyst capable of suscepting microwave radiation in a range 1–20 GHz; mixing an organic compound with elemental nitrogen and a substance selected from the group consisting of oxygen, hydrogen peroxide, argon and helium to form a mixture; and passing the mixture in contact with the catalyst while the catalyst is irradiated with the microwave radiation.

* * * * *